US006597171B2

United States Patent
Hurlimann et al.

(10) Patent No.: US 6,597,171 B2
(45) Date of Patent: Jul. 22, 2003

(54) NUCLEAR MAGNETIC RESONANCE METHODS FOR EXTRACTING INFORMATION ABOUT A FLUID IN A ROCK

(75) Inventors: Martin D. Hurlimann, Ridgefield, CT (US); Olivier J. Terneaud, Saint Avertin (FR); Denise Freed, Mount Kisco, NY (US); Ulrich Scheven, Bethel, CT (US); Lalitha Venkataramanan, Stamford, CT (US)

(73) Assignee: Schlumberger Technology Corporation, Ridgefield, CT (US)

( * ) Notice: Subject to any disclaimer, the term of this patent is extended or adjusted under 35 U.S.C. 154(b) by 0 days.

(21) Appl. No.: 09/909,665

(22) Filed: Jul. 20, 2001

(65) Prior Publication Data

US 2002/0105326 A1 Aug. 8, 2002

Related U.S. Application Data

(60) Provisional application No. 60/220,053, filed on Jul. 21, 2000.

(51) Int. Cl.[7] .................................................. G01V 3/00
(52) U.S. Cl. ...................................... 324/303; 324/300
(58) Field of Search ............................... 324/303, 300, 324/307, 309, 318, 322; 335/296; 600/410

(56) References Cited

U.S. PATENT DOCUMENTS 5,023,551 A 6/1991 Kleinberg et al. .......... 324/303
5,381,092 A 1/1995 Freedman .................. 324/303
5,486,762 A 1/1996 Freedman et al. .......... 324/303
5,936,405 A 8/1999 Prammer et al. ........... 324/303

FOREIGN PATENT DOCUMENTS

GB          2 342 170      4/2000    ............ G01V/3/32
WO      WO01/42817 A1    6/2001    ............ G01V/3/32

OTHER PUBLICATIONS

Hurlimann et al. "Restricted Diffusion in Sedimentary Rocks. Determination of Surface–Area–to–Volume Ratio and Surface Relaxivity." *Journal of Magnetic Resonance, Series A 111* (1994) pp. 169–178.
Journal of the American Chemical Society, 91:27, (1969), pp. 7784–7785, E. D. Becker et al., "A New Method for Nuclear Magnetic Resonance Enhancement".
Journal of Magnetic Resonance, 8, (1972), pp. 298–310, R. R. Shoup et al., "The Driven Equilibrium Fourier Transform NMR Technique: An Experimental Study".

(List continued on next page.)

Primary Examiner—Edward Lefkowitz
Assistant Examiner—Brij B. Shrivastav
(74) Attorney, Agent, or Firm—Jody Lynn DeStefanis; William B. Batzer; John J. Ryberg

(57) ABSTRACT

Nuclear magnetic resonance methods for extracting information about a fluid in a rock are described. A system of nuclear spins in the fluid are prepared in a driven equilibrium, and a series of magnetic resonance signals generated from the fluid. The series of magnetic resonance signals is detected and analyzed to extract information about the fluid in the rock.

32 Claims, 6 Drawing Sheets

OTHER PUBLICATIONS

Journal of Magnetic Resonance, 17, (1975), pp. 295–300, R. J. Kurland et al., "The Half–Wave Triplet Pulse Sequence for Determination of Longitudinal Relaxation Rates of Single Line Spectra".

Journal of Magnetic Resonance, 17, (1975), pp. 301–313, H. T. Edzes, "An Analysis of the Use of Pulse Multiplets in the Single Scan Determination of Spin–Lattice Relaxation Rates".

Journal of Molecular Spectroscopy, 35, (1970), pp. 298–305, J. S. Waugh, "Sensitivity in Fourier Transform NMR Spectroscopy of Slowly Relaxing Systems".

SDR Research Note RDE (2001), Y–Q Song et al., "$T_1$–$T_2$ Correlation Spectra Obtained Using a Fast Two–Dimensional Laplace Inversion".

Siam J. Numerical Analysis, vol. 8, No. 3, (1981), pp. 381–397, J. P. Butler et al., "Estimating Solutions of First Kind Integral Equations with Nonnegative Constraints and Optimal Smoothing".

NUCLEAR MAGNETIC RESONANCE METHODS FOR EXTRACTING INFORMATION ABOUT A FLUID IN A ROCK

This patent application claims priority from U.S. Provisional Patent Application No. 60/220,053 filed Jul. 21, 2000, which is herein incorporated by reference in its entirety.

FIELD OF THE INVENTION

This invention relates to investigations of rock samples, and more particularly relates to nuclear magnetic resonance (NMR) methods for determining characteristics of a fluid in a rock or earth formation.

BACKGROUND

NMR has been a common laboratory technique for over forty years and has become an important tool in formation evaluation. General background of NMR well logging can be found, for example, in U.S. Pat. No. 5,023,551 to Kleinberg et al., which is assigned to the same assignee as the present invention and herein incorporated by reference in its entirety.

NMR relies upon the fact that the nuclei of many chemical elements have angular momentum ("spin") and a magnetic moment. In an externally applied static magnetic field, the spins of nuclei align themselves along the direction of the static field. This equilibrium situation can be disturbed by a pulse of an oscillating magnetic field (e.g., a RF pulse) that tips the spins away from the static field direction. The angle through which the spins are tipped is given by $\theta=\gamma B_1 t_p/2$, where $\gamma$ is the gyromagnetic ratio, $B_1$ is the linearly polarized oscillating field strength, and $t_p$ is the duration of the pulse. Tipping pulses of ninety and one hundred eighty degrees are most common.

After tipping, two things occur simultaneously. First, the spins precess around the direction of the static field at the Larmor frequency, given by $\omega_0=\gamma B_0$, where $B_0$ is the strength of the static field and $\gamma$ is the gyromagnetic ratio. For hydrogen nuclei, $\gamma/2\pi=4258$ Hz/Gauss, so, for example, in a static field of 235 Gauss, the hydrogen spins would precess at a frequency of 1 MHz. Second, the spins return to the equilibrium direction according to a decay time, $T_1$, which is known as the spin-lattice relaxation time. Because this spin-lattice relaxation occurs along the equilibrium direction, $T_1$ is also referred to as the longitudinal relaxation time constant.

Also associated with the spin of molecular nuclei is a second relaxation time, $T_2$, called the spin-spin relaxation time. At the end of a ninety-degree tipping pulse, all the spins are pointed in a common direction perpendicular, or transverse, to the static field, and they all precess at the Larmor frequency. However, because of small fluctuations in the static field induced by other spins or paramagnetic impurities, the spins precess at slightly different frequencies, and the transverse magnetization dephases with a time constant $T_2$, which is also referred to as the transverse relaxation time constant.

A standard technique for measuring $T_2$, both in the laboratory and in well logging, uses a RF pulse sequence known as the CPMG (Carr-Purcell-Meiboom-Gill) sequence. As is well known, after a wait time that precedes each pulse sequence, a ninety-degree pulse tips the spins into the transverse plane and causes the spins to start precessing. Then, a one hundred eighty-degree pulse is applied that keeps the spins in the measurement plane, but causes the spins, which are dephasing in the transverse plane, to reverse direction and to refocus. By repeatedly reversing the spins using a series of one hundred eighty degree pulses, a series of "spin echoes" appear. The train of echoes is measured and processed to determine the irreversible dephasing time constant, $T_2$. In well logging applications, the detected spin echoes have been used to extract oilfield parameters such as porosity, pore size distribution, and oil viscosity.

In theory, other laboratory NMR measurements may be applied in well-logging to extract additional information about the oilfield, but in practice, the nature of well-logging and the borehole environment make implementing some laboratory NMR measurements difficult. For example, inversion recovery is a common laboratory technique for measuring $T_1$. In an inversion recovery measurement, a one-hundred eighty degree pulse is applied to a system of spins aligned along the static magnetic field in order to reverse the direction of the spins. The system of spins thus perturbed begins to decay toward their equilibrium direction according to $T_1$. To measure the net magnetization, a ninety-degree pulse is applied to rotate the spins into the transverse plane and so induce a measurable signal. The signal will begin to decay as the spins dephase in the transverse plane, but the initial amplitude of the signal depends on the "recovery time" between the one-hundred eighty degree pulse and the ninety-degree pulse. By repeating this experiment for different recovery times and plotting the initial amplitude of the signal against recovery time, $T_1$ may be determined. While this technique has been successfully used in the laboratory for several years, inversion recovery is very time consuming, and those of ordinary skill in the art recognize that inversion recovery may be unsuitable for well logging applications.

Accordingly, there continues to be a general need for improved NMR measurements and, in particular for the oil and gas exploration industries, improved NMR methods that can be used to extract information about rock samples and be used in well-logging applications.

SUMMARY OF INVENTION

The invention provides a method for extracting information about a fluid that may be contained in rock or within a portion of earth formation surrounding a borehole (as used hereinafter, the term "rock" includes earth, earth formation, and a portion of earth formation). In one embodiment, the method involves applying a sequence of magnetic pulses to a fluid in a rock. The sequence includes a first part that is designed to prepare a system of nuclear spins in the fluid in a driven equilibrium followed by a second part that is designed to generate a series of magnetic resonance signals. The series of magnetic resonance signals is detected and analyzed to extract information about the fluid in the rock.

Further details and features of the invention will become more readily apparent from the detailed description that follows.

BRIEF DESCRIPTION OF FIGURES

The invention will be described in more detail below in conjunction with the following Figures, in which.

DETAILED DESCRIPTION

Figure 1:
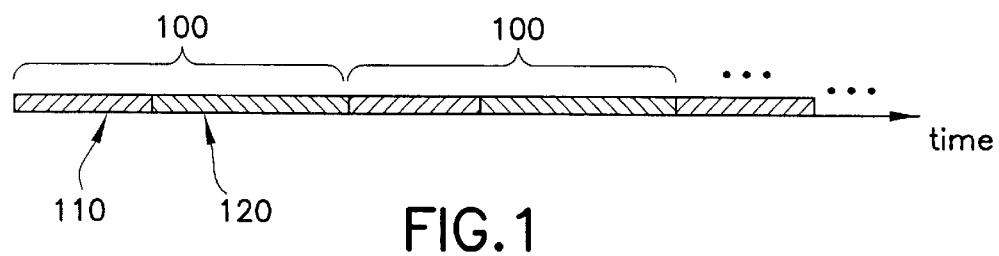
FIG. 1 schematically represents a magnetic field pulse sequence that may be used in accordance with the invention.

FIG. 1 schematically represents a sequence of magnetic field pulses, such as RF pulses, that may be applied to a system of nuclear spins, such as in a fluid in a rock, in accordance with the invention. The magnetic field pulse sequence 100 includes two parts. A first part 110 prepares a system of nuclear spins in a first state. A second part 120 generates from the system of spins a series of magnetic resonance signals. As shown in FIG. 1, the magnetic field pulse sequence 100 may be repeatedly applied, and the magnetic resonance signals detected and combined to build up signal-to-noise.

In generating the series of magnetic resonance signals, the first and second parts preferably excite spins at about the same frequency range. For example, a standard CPMG sequence with a series of 180-degree pulses tends to refocus on-resonance spins, namely those spins having a frequency substantially equal to the Larmor frequency, and the observed CPMG signal primarily includes such on-resonance spins. Accordingly, a standard CPMG sequence would be preferably paired with a first part that also primarily excites on-resonance spins. For a first part that affects primarily off resonance spins, such as a constant RF irradiation (discussed below), the second part preferably is designed to excite substantially the same off-resonance spins. A CPMG-like sequence, in which composite pulses designed to refocus the off-resonance spins replace the 180-degree pulses, may be used in such magnetic pulse sequences. Those of skill in the art will be able to design other types of refocusing sequences to refocus spins having different off-resonance frequencies.

Figure 2:
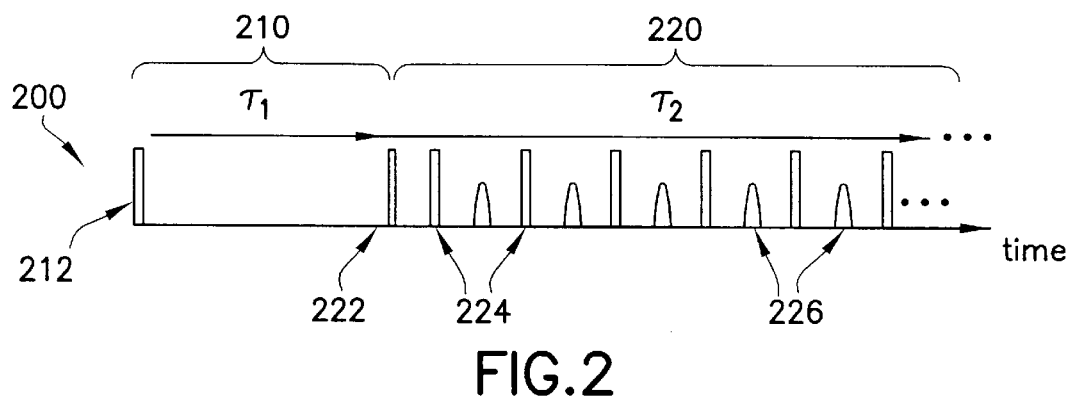
FIG. 2 illustrates an inversion recovery-CPMG sequence.

For example, FIG. 2 shows a magnetic field pulse sequence 200 that includes an inversion recovery sequence 210 followed by a CPMG sequence 220. The inversion recovery sequence includes a 180-degree pulse 212 that reverses the direction of the system of spins, followed by a recovery time, $\tau_1$. After the recovery time, which is typically less than $T_1$, the CPMG sequence 220 is applied, with a 90-degree pulse 222 that rotates the spins into the transverse plane and a series of 180-degree pulses (two of which are indicated by 224) that generates a series of spin echoes (two of which are indicated by 226) whose amplitude depends on $T_1$ and whose decay depends on the transverse relaxation time constant, $T_2$:

$$M(\tau_1, \tau_2) = M_0 \int\int dT_1 dT_2 f(T_1, T_2)\left(1 - 2e^{\frac{-\tau_1}{T_1}}\right)e^{\frac{-\tau_2}{T_2}}, \quad (1)$$

where $T_1$, $T_2$ and, $\tau_1$ are as defined above, $M_0$ is the net magnetization of the spins at thermal equilibrium, $\tau_2$ is the time from the start of the CPMG sequence, and $f(T_1,T_2)$ is the two dimensional density function for $T_1$ and $T_2$.

Another example of a magnetic field pulse sequence that may be used in accordance with the invention includes a first part that is designed to prepare the system of spins in a driven equilibrium state. In general, any magnetic field pulse sequence that repeatedly rotates the net magnetization of the system between the longitudinal and the transverse directions will create a sizable driven equilibrium magnetization. As long as the repeating magnetic field pulse units are short compared to $T_1$ and $T_2$, it can be shown that the resulting equilibrium magnetization depends on a function of the ratio, $T_1/T_2$:

$$M_{eq} = g\left(\frac{T_1}{T_2}\right)M_0. \quad (2)$$

After the spins are prepared in a driven equilibrium, a second part designed to refocus the spins of the system is applied. The second part generates a series of magnetic resonance signals that depends on both the $T_1/T_2$ ratio and $T_2$:

$$M_{de}(\tau_2) = M_0 \int\int dT_2 d\frac{T_1}{T_2} f\left(T_2, \frac{T_1}{T_2}\right) g\left(\frac{T_1}{T_2}\right) e^{\frac{-\tau_2}{T_2}}. \quad (3)$$

$T_1$, $T_2$, and $\tau_2$ are as defined previously, and $$f\left(T_2, \frac{T_1}{T_2}\right)$$

is the two dimensional density function for the ratio $T_1/T_2$ and $T_2$.

Figure 3:
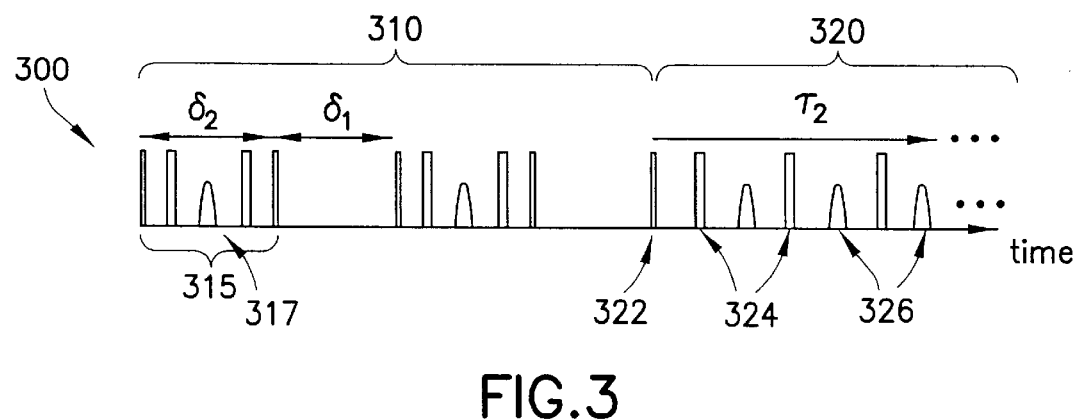
FIG. 3 illustrates one embodiment of a driven equilibrium-refocusing sequence according to the invention.

FIG. 3 illustrates one example of such a driven equilibrium-refocusing sequence. The magnetic field pulse sequence 300 includes a driven equilibrium Fourier transform (DEFT) sequence 310 followed by a CPMG sequence 320. The DEFT sequence 310 shown may be thought of as a repeating block 315 of magnetic field pulses generated according to:

$$[90_{+x} - t_1 - 180_y - t_2 - 180_y - t_1 - 90_{-x}]_i \quad (4),$$

where $t_1$ and $t_2(\approx 2t_1)$ are time spacings between magnetic pulses. Each repeating block is separated by a time, $\delta_1$, and each block has a total width of $\delta_2$. FIG. 3 shows the sequence having two repeating blocks (i=2); however those of skill in the art will recognize that the sequence may have any number of repeating blocks. In many applications, it may be desirable to apply the DEFT sequence for a period of time longer than $T_1$. A magnetic resonance spin echo 317 appears midway between the two $180_y$-degree pulses of each block. Over time, the DEFT sequence prepares the system of spins in a driven equilibrium in which the magnetization, in the limit that $\delta_1 << T_1$ and $\delta_2 << T_2$, is given as:

$$M_{eq} \to \frac{M_0}{1 + \frac{\delta_2}{\delta_1} \frac{T_1}{T_2}}. \quad (5)$$

The asymptotic expression in equation (5) offers a good approximation for the DEFT driven equilibrium magnetization for all parameters in the range of about $T_2/\delta_2 \geq 10$. After the system of spins is prepared in a driven equilibrium, a CPMG sequence 320 is applied, with a 90-degree pulse 322 followed by a series of 180-degree pulses (two of which are indicated by 324) to generate a series of magnetic resonance spin echoes (two of which are indicated by 326) whose signal can be written as equation (3) above, where the function $$g\left(\frac{T_1}{T_2}\right)$$

is given by:

$$g\left(\frac{T_1}{T_2}\right) = \frac{1}{1 + \frac{\delta_2}{\delta_1} \frac{T_1}{T_2}}, \quad (6)$$

which is most sensitive to changes in $T_1/T_2$ in the region where $(\delta_1/\delta_2) \approx <T_1/T_2>$.

Another example of a driven equilibrium-refocusing magnetic field pulse sequence uses a constant RF field, typically applied for a time greater than $T_1$, to prepare the system of spins in a driven equilibrium that depends on the $T_1/T_2$ ratio. The constant RF field typically has a sufficiently high frequency, $\omega_1$, such that $\omega_1 T_2 \gg 1$, in which case the equilibrium magnetization along the y- and z-axes, respectively, are given by:

$$M_{eq,y} = \frac{\frac{\Delta\omega_0}{\omega_1}}{\left(\frac{\Delta\omega_0}{\omega_1}\right)^2 + \frac{T_1}{T_2}} M_0 \quad (7)$$

$$M_{eq,z} = \frac{\left(\frac{\Delta\omega_0}{\omega_1}\right)^2}{\left(\frac{\Delta\omega_0}{\omega_1}\right)^2 + \frac{T_1}{T_2}} M_0. \quad (8)$$

$T_1$, $T_2$, $\omega_1$ and $M_0$ are as defined previously, and $\Delta\omega_0$ is the difference between the frequency of the applied RF field and the Larmor frequency of the spins. From equations (7) and (8), it can be seen that on resonance, i.e., where the frequency of the applied RF field equals the Larmor frequency ($\Delta\omega_0=0$), the equilibrium magnetization vanishes. At $\Delta\omega_0 = \pm\omega_1$, the equilibrium magnetization along both the y- and z-axes becomes $$\frac{M_0}{1 + (T_1/T_2)},$$

which is equivalent to the DEFT equilibrium magnetization for $\delta_1 = \delta_2$ (see equation (5) above). In order to measure the $T_2$ decay of this equilibrium magnetization, a CPMG-like sequence made up of a series of composite pulses designed to refocus off-resonance spins preferably follows the constant RF irradiation. For example, spins having a magnetization around $\Delta\omega_0 = \pm\omega_1$ may be effectively refocused using a CPMG-like series of composite pulses of $127_x-127_{-x}$ degrees, generating a series of spin echoes according to equation (3) above, where the function $g(T_1/T_2)$ is given by $$\frac{1}{1 + (T_1/T_2)}.$$

Figure 4A:
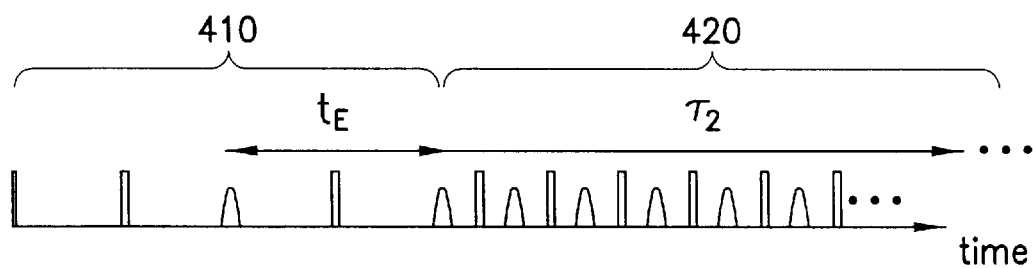
FIGS. 4A and 4B illustrate embodiments of a diffusion editing-CPMG sequence according to the invention.
Figure 4B:
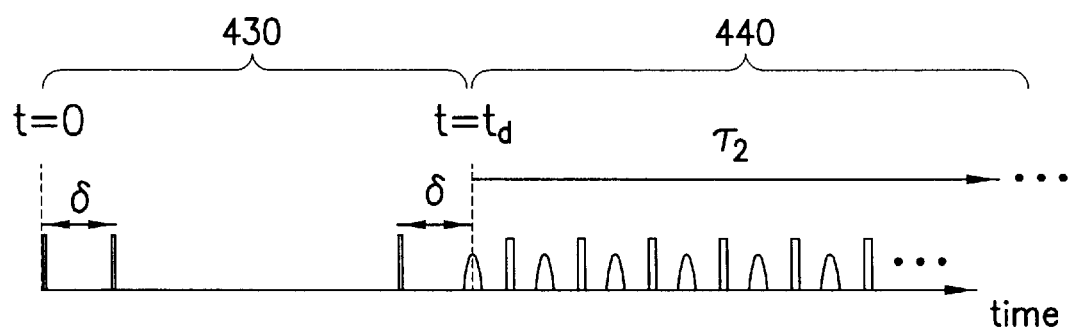

Another type of magnetic field pulse sequence that may be used in accordance with the invention includes a first part that prepares a system of spins with a net magnetization that depends on a diffusion coefficient. A CPMG sequence typically follows the first part and generates a series of magnetic resonance spin echoes that generally decays according to:

$$M(\tau_1, \tau_2) \approx \int\int dDdT_2 e^{\frac{-D\gamma^2 g^2 \tau_1^3}{6}} e^{\frac{-\tau_2}{T_2}} f(D, T_2), \quad (9)$$

where D is the diffusion coefficient, $\tau_1$ is a time associated with the first part, $\gamma$ is the gyromagnetic ratio, g is the gradient field strength, and $\tau_2$ is the time from the start of the CPMG sequence. For example, according to one embodiment shown in FIG. 4A, the first part 410 includes two spin echoes separated by an elongated echo spacing, $t_E$, followed by a standard CPMG sequence of 180-degree pulses 420, and $\tau_1^3 = t_E^3$. According to another embodiment shown in FIG. 4B, the first part 430 includes a stimulated echo sequence characterized by a time spacing $\delta$ and a stimulated echo appearing at time $t_d$, the second part 440 includes a standard CPMG sequence of 180-degree pulses, and $\tau_1^3 = 6t_d\delta^2$. Diffusion editing magnetic field pulse sequences are described in more detail in U.S. patent application Ser. No. 09/723,803, which is incorporated herein by reference.

Figure 5:
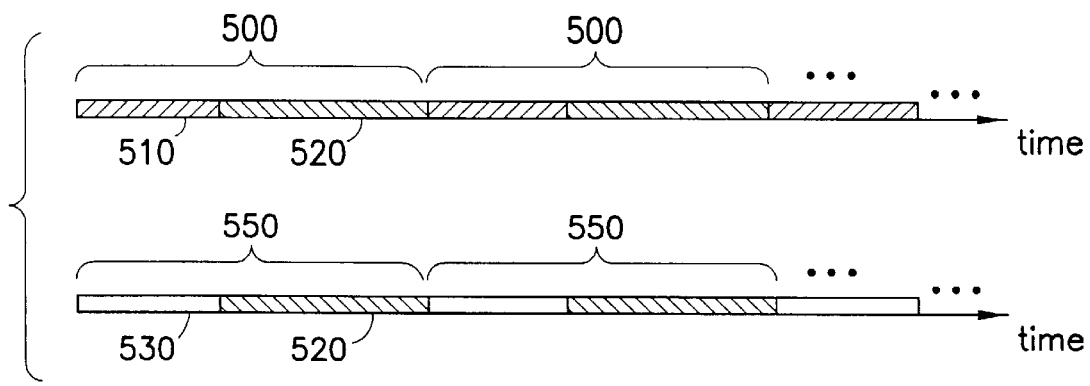
FIG. 5 schematically illustrates one embodiment of a nuclear magnetic resonance measurement according to the invention.

FIG. 5 schematically illustrates one embodiment of a nuclear magnetic resonance measurement according to the invention that involves preparing a system of spins in the fluid with different initial conditions and then measuring the decay of the spins from the different initial conditions using the same refocusing sequence. A first sequence 500 that includes a first part 510 followed by a second part 520 is applied to the fluid to generate a first series of magnetic resonance spin echoes. A second sequence 550 that includes a third part 530 followed by the second part 520 is applied to generate a second series of magnetic resonance spin echoes. The first and second series of magnetic resonance spin echoes are detected and analyzed to extract information about the fluid in the rock. Additional sequences (not shown) may be applied to the system of spins to prepare the system in a plurality of different initial conditions from which additional series of magnetic resonance spin echoes may be generated, detected, and analyzed.

As shown in FIG. 5, the first sequence 500 may be applied repeatedly before the second sequence 550 is applied to the fluid. The second sequence 550, as shown in FIG. 5, also may be applied repeatedly. The magnetic field pulses of each sequence may be phase-cycled to help reduce noise due to mismatched pulses. Those of ordinary skill in the art will recognize that phase-cycling may be performed by varying the phase of magnetic field pulses within a given sequence or by varying the phase of magnetic field pulses from sequence to sequence.

The first sequence 500 encompasses the magnetic field pulse sequences described above, and so includes sequences having a first part 510 that prepares the spins initially in a first state with a magnetization that depends on a first parameter, such as $T_1$, $T_1/T_2$, D, etc. The second sequence 550 prepares the spins initially in a second state that is different than the first state, and may include the magnetic field pulse sequences described above to prepare the spins with a magnetization that has a different dependence on the first parameter. Alternatively, the third part 530 may include a wait time longer than a longitudinal relaxation time constant, $T_1$, during which no magnetic field pulses are applied to the fluid. The wait time allows the spins to reach a thermal equilibrium with the static magnetic field, $B_0$.

The same refocusing sequence 520 is used in both the first and the second sequences to generate magnetic resonance signals from the different initial conditions. Where the third part includes a wait time and the second part includes a CPMG or CPMG-like sequence, the magnetic resonance signal generated by the second sequence may be expressed generally as a standard CPMG expression, which depends on one parameter, $T_2$:

$$M_{te}(\tau_2) \approx \int dT_2 f(T_2) e^{\frac{-\tau_2}{T_2}}, \qquad (10)$$

The second part 520 is preferably, though not necessarily, applied for substantially the same duration in both the first and the second sequences so as to generate substantially the same number of spin echoes in each the first and second series.

Figure 6:
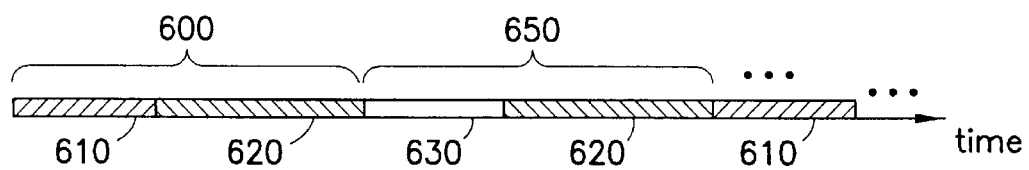
FIG. 6 schematically illustrates an alternative embodiment of a nuclear magnetic resonance measurement according to the invention.

As shown in FIG. 5, the first sequence 500 may be repeatedly applied and then the second sequence 550 repeatedly applied to the fluid. Alternatively, as shown in FIG. 6, the first and second sequences may be interlaced to allow acquisition of the two magnetic resonance signals during a single pass. The nuclear magnetic resonance measurement shown in FIG. 6 represents an alternative implementation for preparing a system of spins in different states and then measuring the decay of the spins from the different states using the same refocusing sequence, as described above with reference to FIG. 5. A first magnetic field pulse sequence 600 includes a first part 610 to prepare a system of spins in a first state followed by a second part 620 to generate a first series of magnetic spin echoes, and is followed by a second magnetic field pulse sequence 650 that includes a third part 630 to prepare the system in a second state followed by the second part 620 to generate a second series of magnetic spin echoes. The first sequence 600 and the second sequence 650 may be alternated, as shown, and applied repeatedly, with appropriate phase-cycling, to build up signal-to-noise of the first and second series of magnetic spin echoes. Additional sequences may be interlaced with the first and second sequences to prepare the system of spins in a plurality of different initial conditions from which additional series of magnetic resonance spin echoes may be generated, detected, and analyzed.

The magnetic resonance spin echoes generated from magnetic field pulse sequences 500, 550 or 600, 650 are detected and analyzed to extract information about the fluid. For example, the first sequence may be an inversion recovery-CPMG sequence that prepares the spins with a non-equilibrium magnetization that depends on $T_1$ and generates a first series of magnetic resonance spin echoes that depends on $T_1$ and $T_2$ (see equation (1) above), and the second sequence may be an inversion recovery-CPMG sequence with a different recovery time that prepares the spins with a different non-equilibrium magnetization. Such an inversion recovery-CPMG measurement may be repeated a plurality of times, varying the recovery times, and the plurality of series of magnetic resonance spin echoes ana-lyzed in order to extract a two-dimensional $T_1$-$T_2$ distribution, $f(T_1,T_2)$.

Figure 7:
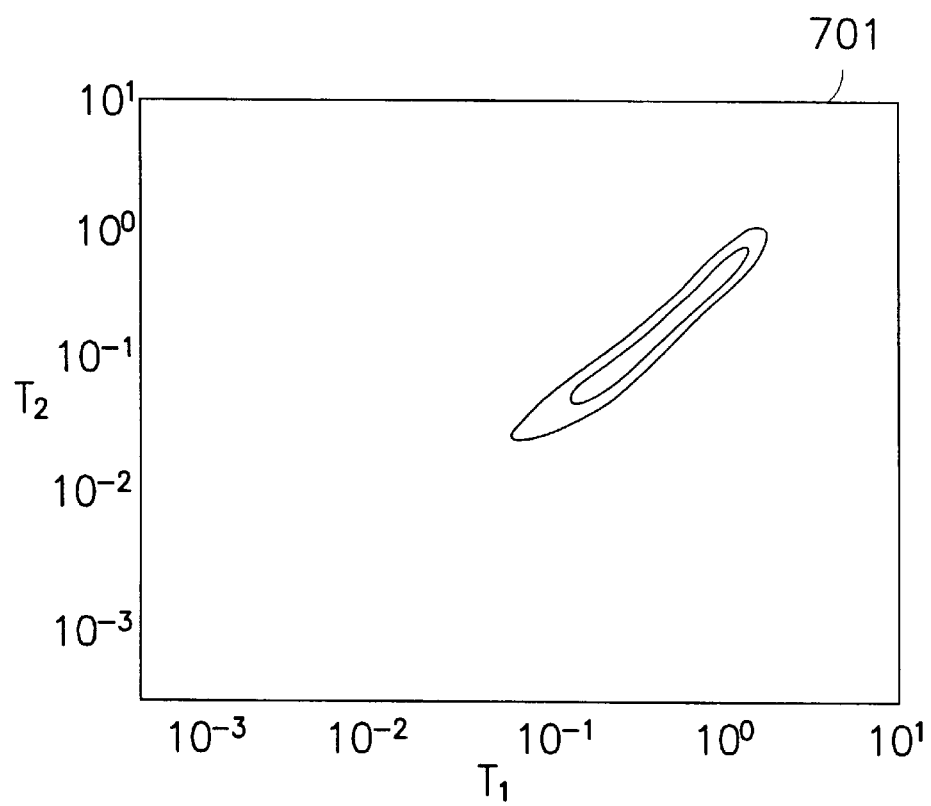
FIG. 7 contains a two-dimensional map of $T_1$ versus $T_2$ of a water-saturated rock sample generated in accordance with the invention.
Figure 8:
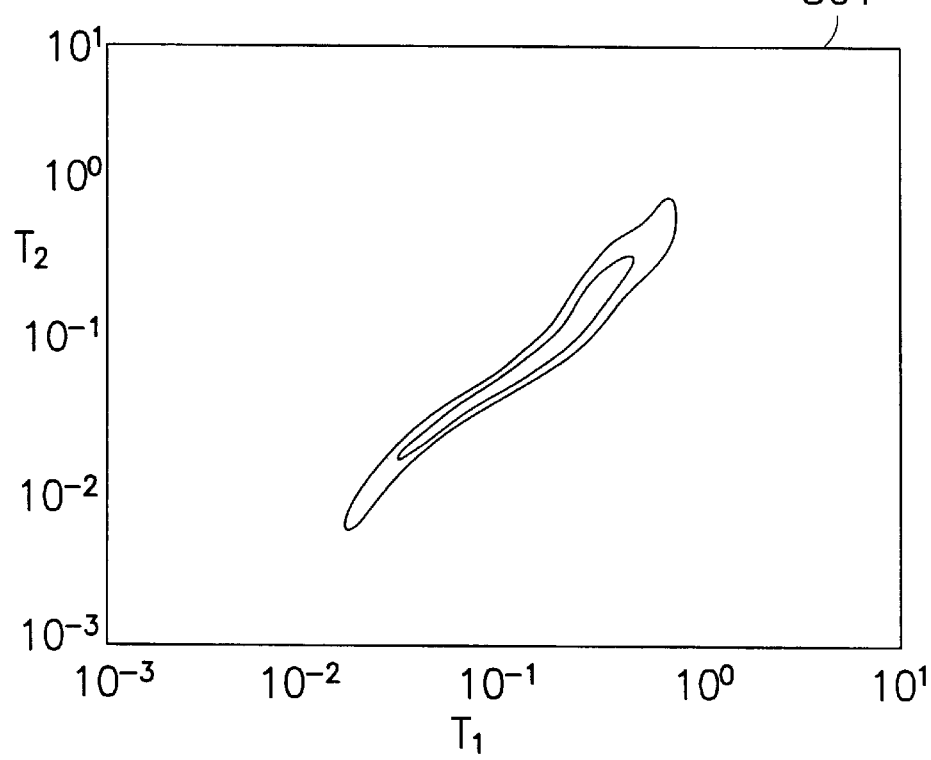
FIG. 8 contains a two-dimensional map of $T_1$ versus $T_2$ of an oil-saturated rock sample generated in accordance with the invention.

FIGS. 7 and 8 contain a two-dimensional map of $T_1$ versus $T_2$ of a water-saturated and an oil-saturated sandstone rock sample, respectively, generated from such a plurality of inversion recovery-CPMG experiments where the recovery time was varied between approximately 100 µs and 10 s. The intensity of the signal at each point on the map provides an indication of the number of spins, and thus the fluid volume, contributing to the signal at that point. $T_1$ conveys potentially useful information. In a bulk fluid, $T_1$ typically equals $T_2$, or $T_1/T_2=1$. A porous environment, such as found in a rock or an earth formation, may introduce additional relaxation effects that affect the longitudinal and transverse relaxation times differently. For example, in a wetting phase, such as in a water-saturated rock, the spins relax predominantly due to collisions with the grain surface, and the longitudinal and transverse relaxation time are affected differently, typically such that $T_1 > T_2$, which is evident in FIG. 7 (the line 701 indicates $T_1=T_2$). In a non-wetting phase, however, such as in an oil phase, surface relaxation is negligible, and the $T_1$ remains approximately equal to $T_2$, i.e. $T_1/T_2 \approx 1$. FIG. 8 shows that for longer $T_2$'s, which sample the larger oil-filled pores, $T_2$ does approximately equal $T_1$ (the line 801 indicates $T_1=T_2$). However, at shorter $T_2$'s, which sample the smaller pores, a layer of water most likely effectively fills the pores and introduces surface relaxation effects that shorten $T_2$ relative to $T_1$. Thus, $T_1$ contains information that may allow wetting and non-wetting phases within a rock formation, e.g., water versus oil, to be distinguished.

Some embodiments of the invention may generate a large number of data points. For example, the plurality of inversion recovery-CPMG experiments described above may generate a million or more data points. To analyze NMR data that may be generated by the methods of the invention in real time and without large computer memory requirements, an inversion method has been developed that takes advantage of the tensor product structure of the kernel (see equations (1), (3) and (9) above). For example, the inversion recovery-CPMG data may be expressed with a kernel that is separable into $k_1 = 1 - 2e^{-\tau_1/T_1}$ and $k_2 = e^{-\tau_2/T_2}$ (see equation (1)); for the driven equilibrium-refocusing data, the kernel is separable into $k_1 = g(T_1/T_2)$ and $k_2 = e^{-\tau_2/T_2}$ (see equation (3)); and for the diffusion editing-CPMG data, the kernel is separable into $k_1 = e^{-D\gamma^2 g^2 \tau_1 3/6}$ and $k_2 = e^{-\tau_2/T_2}$ (see equation (9)).

In implementing the inversion method, each data set is discretized and written in matrix notation:

$$M_r = K_1 F_r K'_2 + E_r, \text{ for } r = 1, \ldots, R \qquad (11),$$

where R is the number of data sets and, for the discretized parameters $x^{(i)}, i=1, \ldots, N_x$ and $y^{(i)}, i=1, \ldots, N_y$, $M_r$ is a matrix containing the r-th data set; matrices $K_1$ and $K_2$ contain entries corresponding to continuous kernels $k_1$ and $k_2$; matrix $F_r$ is the discretized version of a continuous probability density function $f_r(x,y)$; and matrix $E_r$ represents the noise associated with the data. To solve for $F_r$, equation (11) is posed as an optimization problem subject to a non-negativity constraint:

$$\hat{F}_r = \underset{F_r \geq 0}{\arg\min} \|M_r - K_1 F_r K'_2\|^2 + \alpha \|F_r\|^2, r = 1, \ldots, R, \qquad (12)$$

where $\|\cdot\|^2$ denotes the Frobenius norm of a matrix. The first term of equation (12) measures the difference between the data and the fit, and the second term summed over all the data sets, r=1 , ... , R, is a measure of the smoothness of the discretized density function, $F_r$. The parameter, $\alpha$, is a smoothening or regularization parameter that controls the smoothness of the estimated density function $F_r$ along each dimension of the data, including along r=1 , ... , R.

The inversion method involves first compressing the data $M_r$ along each dimension of the kernel using, for example, singular value decomposition of $K_1$ and $K_2$ or one of several averaging schemes known in the art, such as window sums, etc. The tensor product structure of the kernel allows for efficient compression of the data, which tends to be highly redundant. Data compression typically reduces the size of the data at least about a thousand-fold without modifying the structure of the problem, and allows for efficient estimation of the discretized density function $F_r$. In the lower dimensionality space of the compressed data set $\tilde{M}_r$, the density function $F_r$ may be estimated using one of several known methods, such as least squares fitting, Butler-Reed-Dawson (BRD), etc. For example, in applying the BRD method, the constrained optimization problem for estimating $F_r$ (see equation (12) above) is converted into an unconstrained optimization problem for estimating a vector $c_r$, r=1 , ... , R, whose dimension equals the size of the compressed data. The vector $c_r$ may be expressed as:

$$c_r = \frac{\tilde{K}\tilde{F}_r - \tilde{m}_r}{-\alpha}, \quad (13)$$

where $\tilde{K}$ is the tensor product of $\tilde{K}_1$ and $\tilde{K}_2$, which represent the compressed kernels along the first and second dimensions, respectively; and $\tilde{m}_r$ and $\tilde{F}_r$ are vectors obtained by lexicographically ordering matrices $\tilde{M}_r$ and $F_r$, respectively. Once $c_r$ is estimated, the vector $\tilde{F}_r$ may be estimated as $\tilde{F}_r$=max(0, $\tilde{K}'c_r$), from which the matrix $F_r$ may be determined. The optimization is done iteratively until the estimated solution for $F_r$ converges within a desired limit.

As mentioned previously, the smoothening parameter $\alpha$ controls the smoothness of the estimated density function $F_r$ along each dimension of the data, including along r=1 , ... , R. An optimal value of the smoothening parameter $\alpha$ may be determined using one of a number of different strategies known in the art, such as adhoc, BRD, S-curve, cross-validation, Morozov discrepancy principle, minimum-bound, predictive mean square estimation, etc. For example, the application of the BRD method to optimizing $\alpha$ for 2- to 3-dimensional data is an extension of the method described in J. P. Butler, et al., "Estimating Solutions of the First Kind Integral Equations with Nonnegative Constraints and Optimal Smoothing", SIAM J. Numerical Analysis, vol. 18, no. 3, pages 381–397, June 1981.

This inversion method may be applied to any two- to three-dimensional NMR data that may be expressed generally as:

$$M_r(\tau_1,\tau_2) = \int\int k_1(x,\tau_1)k_2(y,\tau_2)f_r(x,y)\,dxdy + E_r(\tau_1,\tau_2), r=1, \ldots, R \quad (14),$$

where $M_r(\tau_1,\tau_2)$ represents the r-th data set; $k_1$ and $k_2$ represent the kernel separated along a first dimension and a second dimension, respectively; $\tau_1$ and $\tau_2$ are a first and a second time, respectively, associated with the nuclear magnetic resonance measurement; x and y are parameters related to the system of spins; $f_r(x,y)$ is a joint probability density function between x and y over the R data sets ($f_r(x,y)$ also may be thought of as a three-dimensional probability density function of x, y, and an independent, experimentally controlled variable, r); and $E_r(\tau_1,\tau_2)$ represents noise associated with the r-th nuclear magnetic resonance data set. In the case where R=1, then the data are two dimensional, and the method described above correspond to a two-dimensional inversion. This inversion technique has applicability beyond the NMR measurements described herein. As applied to two- and 2.5-dimensional data sets, this inversion technique provides a computationally efficient and robust method of extracting a two-dimensional map of any two parameters that may be transformed out of NMR data, such as $T_1$, $T_2$, $T_1/T_2$ ratio, D, viscosity, saturation, etc. Further details of the inversion method are described in Appendix C of U.S. Provisional Application No. 60/220,053, which has been incorporated herein by reference in its entirety.

The inversion recovery-CPMG measurements in conjunction with the inversion method described above is capable of providing a full map of the two-dimensional density function, $f(T_1,T_2)$, with a level of detail that was heretofore not practically achievable, as shown in FIGS. 7 and 8. Other magnetic field pulse sequences and other inversion methods may be used in NMR well-logging applications to provide some of the same information as the inversion recovery-CPMG sequence.

For example, a driven equilibrium-refocusing sequence as described above prepares the system of spins with an equilibrium magnetization that depends on $T_1/T_2$ and then generates a first series of magnetic resonance signals that depends on $T_1/T_2$ and $T_2$ (see equation (3) above). Analyzing the first series of magnetic resonance signals together with a second series of magnetic resonance signals generated, for example, by applying a wait time followed by the refocusing sequence allows an average $T_1/T_2$ ratio, i.e., $<T_1/T_2>$, to be determined. An average $T_1/T_2$ ratio, averaged over all $T_1$ values, or even averaged over all spins, provides some indication of whether a sample contains a wetting phase or a non-wetting phase. Thus the main information contained in the full two-dimensional $T_1$-$T_2$ density function may be extracted in a single pass experiment that would be suitable for use in well-logging applications.

Figure 9:
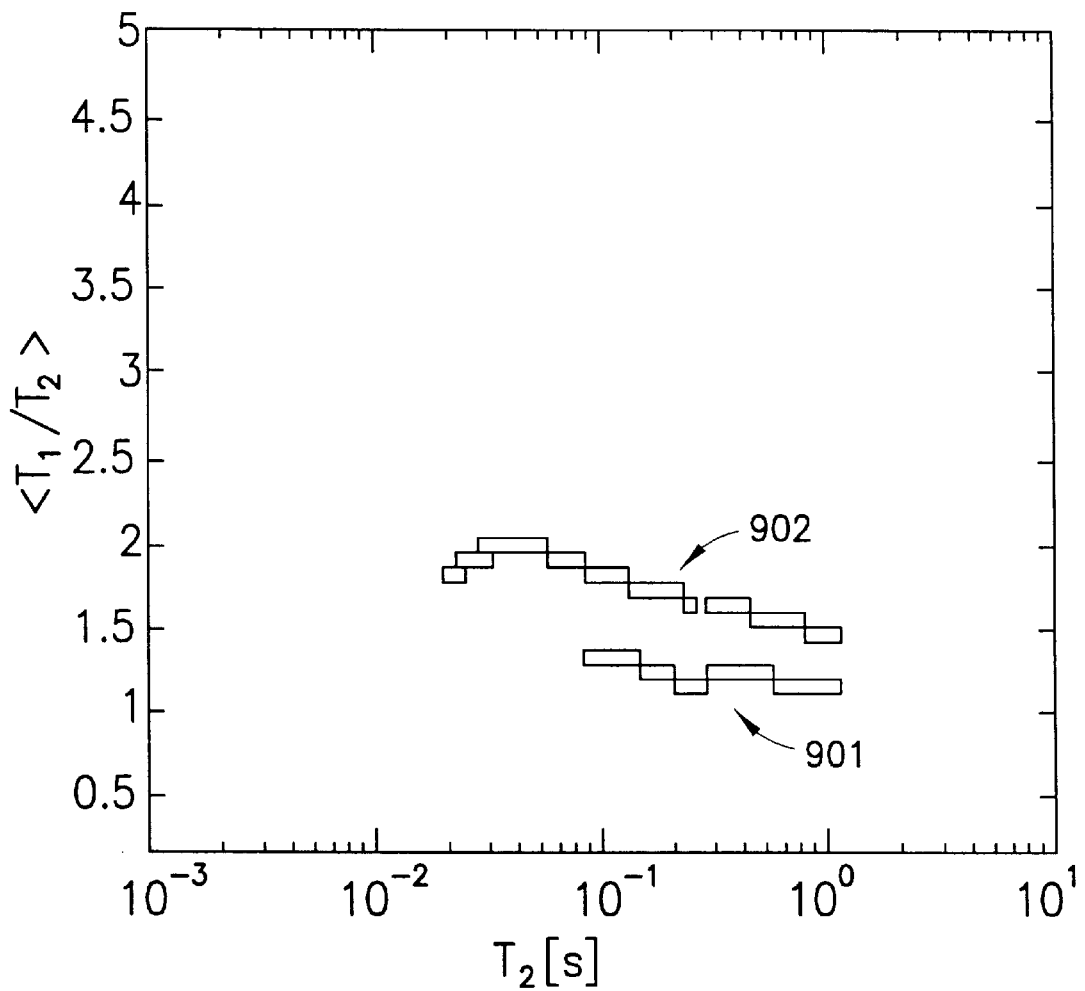
FIG. 9 contains a two-dimensional map of $<T_1/T_2>$ versus $T_2$ of a rock sample generated in accordance with the invention.

FIG. 9 illustrates a two-dimensional map of $<T_1/T_2>$ versus $T_2$ derived from two sandstone samples, one saturated with water and the other partially saturated with water and oil. These maps, which have been superimposed on one plot, were extracted from data generated by a DEFT-CPMG sequence (as given by expression (4) above and as illustrated in FIG. 3) with $\delta_1 = \delta_2 = 400$ μs. By taking a ratio of the DEFT-CPMG data (see equation (3) together with equation (6) above) to the data generated from a standard CPMG (see equation (10) above), the expected value of $$g\left(\frac{T_1}{T_2}\right)$$

was obtained, from which $<T_1/T_2>$ averaged over $T_1$ for each $T_2$ was derived. While not as detailed as the $T_1$-$T_2$ maps shown in FIGS. 7 and 8, a water phase and oil phase are clearly distinguishable in the $<T_1/T_2>$ versus $T_2$ map of FIG. 9 for the water-oil saturated sample 901. For example, looking at $T_2$ components around 200 ms and higher of 901, $<T_1/T_2>$ is approximately 1, indicating the presence of oil. At shorter values of $T_2$, $<T_1/T_2>$ for 901 is clearly greater than 1 and coincides with the $<T_1/T_2>$ versus $T_2$ map for the water saturated sample 902, indicating that the smaller pores of the water-oil saturated sample corresponding to the shorter $T_2$ components are filled with water. The intensity of the signal at each point provides an indication of the number of spins and thus the volume of fluid that contribute to the signal at that point.

The DEFT-CPMG sequence used to generate the $<T_1/T_2>$ versus $T_2$ maps shown in FIG. 9 was implemented with magnetic field pulses about 1 kHz off-resonance. It has been found that, in homogeneous fields, the DEFT-CPMG signal is sensitive to phase and amplitude mismatches in the pulses, so pulse imperfections affect the observed signal. Various phase cycling schemes may be used to reduce the effects of imperfect pulses. The signal sensitivity also may be reduced using magnetic field pulses that are offset from resonance by $\Delta\omega \approx \pm(1/\delta_1)$, and by using two 180-degree pulses in the $\delta_2$ period instead of one. Making these modifications to the DEFT-CPMG sequence resulted in good agreement between the signals measured in the laboratory and equations (3) and (6) above.

In inhomogeneous fields such as is typically found in most well-logging applications, however, some spins are necessarily off-resonance, and, in the fast pulsing limit (i.e., $\tau_1, \tau_2 >> T_1, T_2$), the DEFT-CPMG signal does not exhibit the same sensitivity to pulse imperfections. However, to fit the observed DEFT-CPMG signals to equation (3) together with equation (6) above, all of the off-resonance behavior and the details of the data acquisition (such as signal bandwidth, etc.) are preferably taken into account in calculating $$g\left(\frac{T_1}{T_2}\right).$$

It should be noted that the constant RF irradiation driven equilibrium, being generated by a single pulse, would not be as sensitive to pulse mismatches and pulse imperfections as the DEFT driven equilibrium, and so is well-suited for use with inhomogeneous fields, such as are found in most well-logging applications.

Figure 10:
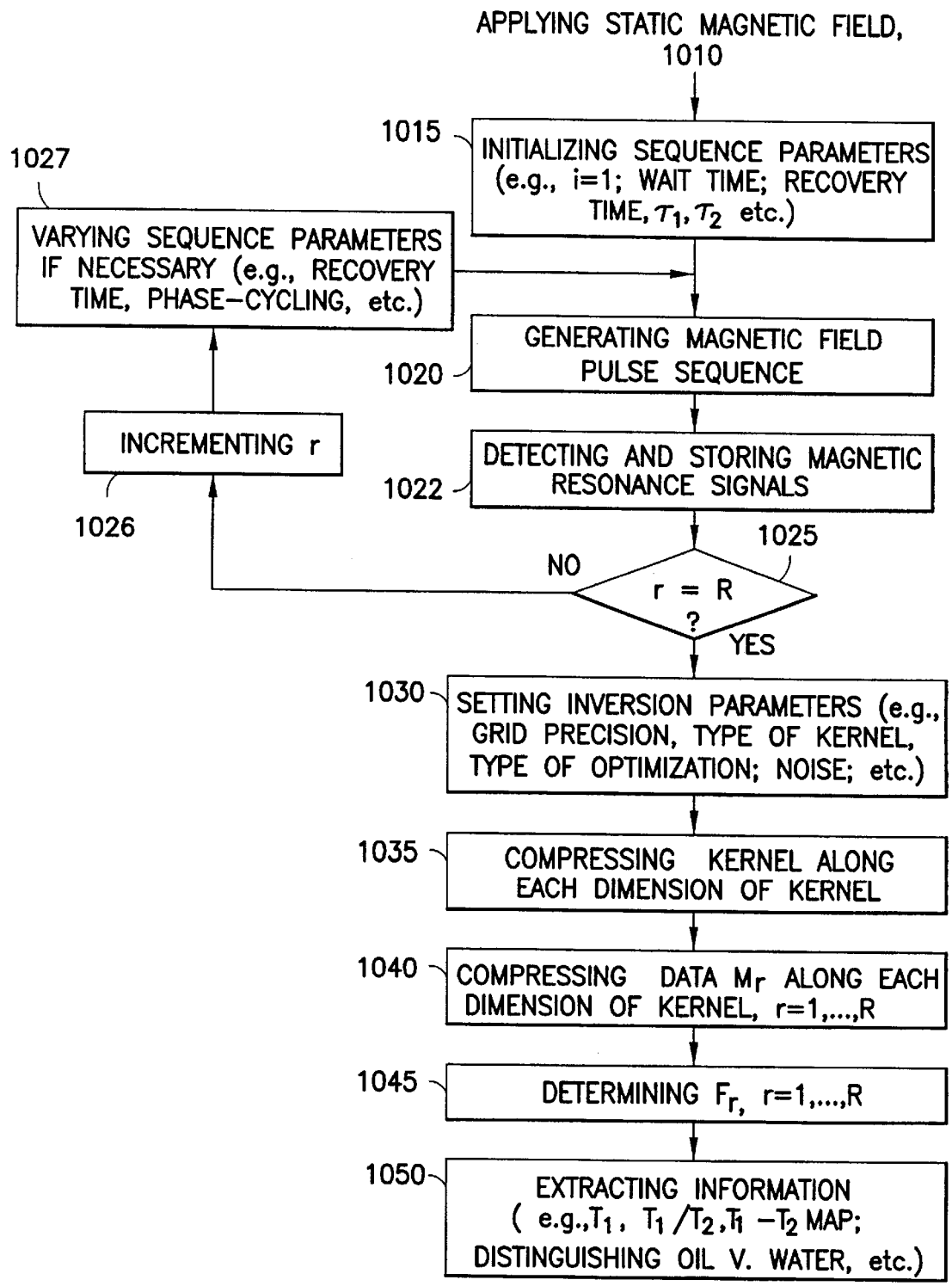
FIG. 10 illustrates a routine that may be used in implementing one embodiment of a method of the invention.

The invention may be implemented in well logging using any nuclear magnetic resonance (NMR) well logging apparatus known in the art. Embodiments of the invention may be implemented with NMR well logging devices without the need for hardware modifications. FIG. 10 shows a flow diagram of a routine that can be used in programming a processor in implementing certain embodiments of the invention. The routine may be stored on or provided over a computer or machine readable medium, such as read-only memory (ROM); random access memory (RAM); magnetic disc or tape; a CD-ROM or other optical storage media; electrical, optical, acoustical or other forms of propagated signals; and the like. The processor may be a downhole processor, an uphole processor, or a combination thereof. The processor also may include a remote processor that may be used for implementing some of the data inversion and interpretation parts of the routine.

Prior to the beginning of the programmed routine and as shown at 1010, a static magnetic field is applied to a region of investigation within an earth formation surrounding a borehole. Theoretically, the earth's magnetic field could be used as the static magnetic field. For most practical purposes, however, this is not preferred. The static magnetic field and field gradient (when desired) typically are applied using a logging tool having a permanent magnet or an array of permanent magnets.

The programmed routine begins at block 1015, which represents initializing parameters for the magnetic field pulse sequence. The sequence parameters may include, for example, i=1, a recovery time, a wait time, $\tau_1$, $\tau_2$, etc., depending on the pulse sequence to be applied. In some embodiments, phase-cycling instructions also may be introduced into the programmed routine at 1015. Generating a magnetic field pulse sequence in the region of investigation is represented by block 1020. Magnetic resonance signals from the region of investigation are detected in block 1022 and stored.

Some embodiments of the invention involve repeatedly applying the magnetic field pulse sequence, or involve applying a plurality of magnetic field pulse sequences. A parameter R may be used (set, perhaps, at block 1015) to indicate a total number of magnetic field pulse sequences to be generated and applied. Decision block 1025 represents querying whether a counter, r, equals R. If no, then r is incremented, as represented in block 1026, and, if necessary, sequence parameters, such as recovery time or phase-cycling instructions, are varied as represented in block 1027, before the routine is returned to block 1020 where the next sequence is generated in the region of investigation. If r=R when queried at decision block 1025, then the data acquisition for the measurement is complete and the routine continues on to block 1030 where the data inversion begins. Depending on the particular NMR measurement being performed, more than one counters and more than one iterative loop may be required.

The data inversion begins at block 1030 by setting the inversion parameters, such as the grid precision to be used in evaluating F, the density distribution; type of kernel; type of optimization, noise, etc. In some embodiments, the kernel and the data are first compressed, and a first objective of the inversion is to extract the density distribution, F, from the data, as shown in blocks 1035 to 1045. Block 1035 represents compressing the kernel along each dimension of the kernel. In cases where the kernel has two dimension, the 2D kernel may be compressed, for example, by first evaluating each 1D kernel with a singular value decomposition and then computing the compressed 2D kernel. Typically, the kernel is compressed one time and applied to each data set, so when the data are compressed at block 1040, the compressed kernel does not need to be calculated again for each data set. The data sets $M_r$, r=1, ..., R, are compressed along each dimension of the kernel at block 1040. The density distribution $F_r$ for r=1, ..., R is determined at 1045. In some embodiments, determining $F_r$ involves posing the problem in an unconstrained optimization framework in a lower dimensionality space (having a dimension equal to that of the compressed kernel) and iteratively optimizing $F_r$ until it converges within a desired limit. When $F_r$ has been determined, information about the region of interest, such as $T_1$, $T_1/T_2$, $T_1$–$T_2$ map, etc., is extracted at block 1050. In some embodiments, information about the region of interest, such as a $<T_1/T_2>$–$T_2$ map, may be extracted without having to fully invert for $f$, as described previously.

The invention allows information about a system of nuclear spins, such as in a fluid in a rock, to be extracted, either in a laboratory setting or in well-logging applications. Some embodiments may be used to extract two-dimensional maps of parameters of interest, such as $T_1$ and $T_2$, $T_1/T_2$ and $T_2$, D and $T_2$, etc., which may prove useful in distinguishing between fluids and/or between different pore environments within a rock. While the invention has been described herein with reference to certain examples and embodiments, it will be evident that various modifications and changes may be made to the embodiments described above without departing from the scope and spirit of the invention as set forth in the claims.

We claim:

1. A method of extracting information about a fluid in a rock comprising:

a) applying a first sequence of magnetic field pulses to the fluid, the sequence comprising a first part designed to prepare a system of nuclear spins in the fluid in a first driven equilibrium followed by a second part designed to generate a series of magnetic resonance signals;

b) detecting the series of magnetic resonance signals from the fluid;

c) applying a second sequence of magnetic field pulses to the fluid, the second series comprising a third part that follows the second part, the third part being designed to prepare the system in a different driven equilibrium state and being followed by the second part to generate a second series of magnetic resonance signals;

d) detecting the second series of magnetic resonance signals from the fluid;

e) analyzing the first and second series of magnetic resonance signals to extract information about the fluid in the rock.

2. The method of claim 1, wherein the system of spins in the first driven equilibrium has an equilibrium magnetization that depends on a function of $T_1/T_2$.

3. The method of claim 1, wherein the first part comprises a DEFT sequence.

4. The method of claim 1, wherein the first part comprises a constant radio-frequency field.

5. The method of claim 1, wherein the second part is designed to refocus spins having substantially similar frequencies as spins in the first driven equilibrium.

6. The method of claim 1, wherein the second part comprises a series of 180-degree pulses.

7. The method of claim 1, wherein the second part comprises a series of composite magnetic field pulses.

8. The method of claim 1, further comprising repeating steps a), b), c) and d) a plurality of times.

9. The method of claim 8, further comprising phase-cycling the sequence of magnetic field pulses before repeating step a).

10. The method of claim 1, wherein the third part further comprises a wait time wherein no magnetic field pulses are applied.

11. The method of claim 10, wherein the wait time is greater than a longitudinal relaxation time associated with the fluid.

12. The method of claim 10, wherein the second part of the first sequence is applied for substantially similar durations after the first part of the first sequence and after the wait time.

13. The method of claim 1, wherein analyzing the series of magnetic resonance signals comprises extracting a ratio of $T_1/T_2$.

14. The method of claim 13, further comprising using the ratio of $T_1/T_2$ to distinguish between oil and water in the fluid in the rock.

15. A method of extracting information about a fluid in a rock comprising:

a) preparing a system of nuclear spins in a driven equilibrium and then generating a first series of magnetic resonance signals from the system;

b) preparing the system of nuclear spins in a thermal equilibrium and then generating a second series of magnetic resonance signals from the system;

c) detecting the first and second series of magnetic resonance signals; and d) analyzing the first and second series of magnetic resonance signals to extract information about the fluid in the rock.

16. The method of claim 15, wherein preparing the system of nuclear spins in the driven equilibrium comprises applying a sequence of magnetic field pulses to the fluid, the sequence being designed to repeatedly rotate a net magnetization associated with the system between a longitudinal direction and a transverse direction.

17. The method of claim 16, wherein the sequence of magnetic field pulses comprises a DEFT sequence.

18. The method of claim 15, wherein preparing the system of nuclear spins in the driven equilibrium comprises applying a constant radio-frequency field to the fluid.

19. The method of claim 15, wherein preparing the system of nuclear spins in the thermal equilibrium comprises not applying any magnetic field pulses to the fluid for a period of time.

20. The method of claim 19, wherein the period of time is longer than a longitudinal relaxation time associated with the system of spins.

21. The method of claim 15, wherein generating the first series of magnetic resonance signals comprises applying a CPMG sequence of magnetic field pulses to the fluid.

22. The method of claim 21, wherein generating the second series of magnetic resonance signals comprises applying the CPMG sequence to the fluid.

23. The method of claim 15, wherein generating the first series of magnetic resonance signals comprises applying a CPMG-like sequence of magnetic field pulses to the fluid.

24. The method of claim 23, wherein the CPMG-like sequence comprises a series of composite pulses.

25. The method of claim 23, wherein generating the second series of magnetic resonance signals comprises applying the CPMG-like sequence to the fluid.

26. The method of claim 15, wherein steps a) and b) are repeated a plurality of times.

27. The method of claim 15, wherein analyzing the first and second series of magnetic resonance signals comprises comparing the first series of magnetic resonance signals to the second series of magnetic resonance signals.

28. The method of claim 27, wherein analyzing the first and second series of magnetic resonance signals further comprises extracting an average $T_1/T_2$ ratio.

29. The method of claim 15, wherein analyzing the first and second series of magnetic resonance signals comprises:

i) compressing the first and second series of magnetic resonance signals; and ii) analyzing the compressed data in an unconstrained optimization framework.

30. The method of claim 29, wherein analyzing the compressed data comprises determining a two-dimensional density function of $T_1/T_2$ and $T_2$.

31. A logging apparatus comprising:

a logging tool that is moveable through a borehole; and a processor coupled with the logging tool, the processor being programmed with instructions which, when executed by the processor, cause the logging tool to:

a) apply a first and second sequence of magnetic field pulses to a region of investigation of an earth formation surrounding the borehole, the first sequence comprising a first part designed to prepare a system of nuclear spins in the region of investigation in a driven equilibrium followed by a second part that generates a first series of magnetic resonance spin echoes, the second sequence comprising a third part that follows the second part, the third part being designed to prepare the system in a different driven equilibrium state and being followed by the second part to generate a second series of magnetic resonance signals;

b) detect the first and second series of magnetic resonance signals from the region of investigation; and cause the processor to:

c) analyze the first and second series of magnetic resonance signals to extract information about the fluid in the rock.

32. A logging apparatus comprising:

a logging tool that is moveable through a borehole; and a processor coupled with the logging tool, the processor being programmed with instructions which, when executed by the processor, cause the logging tool to:

a) prepare a system of nuclear spins within a region of investigation of an earth formation surrounding the borehole in a driven equilibrium and then generate a first series of magnetic resonance signals from the system;

b) prepare the system of nuclear spins in a thermal equilibrium and then generate a second series of magnetic resonance signals from the system;

c) detect the first and second series of magnetic resonance signals; and cause the processor to:

d) analyze the first and second series of magnetic resonance signals to extract information about the fluid in the rock.

* * * * *